United States Patent
Feola et al.

(12)

(10) Patent No.: US 8,206,930 B2
(45) Date of Patent: Jun. 26, 2012

(54) **COMPOSITIONS AND METHODS FOR DETECTING *BORRELIA AFZELII***

(75) Inventors: Melanie Feola, Cherry Hill, NJ (US);
Martin Adelson, East Windsor, NJ (US);
Eli Mordechai, Robbinsville, NJ (US);
Lisa Novak, Miami, FL (US)

(73) Assignee: Medical Diagnostics Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/199,093

(22) Filed: Aug. 18, 2011

(65) Prior Publication Data

US 2012/0122092 A1    May 17, 2012

Related U.S. Application Data

(63) Continuation of application No. 12/156,029, filed on May 29, 2008, now Pat. No. 8,026,056.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |

(52) U.S. Cl. ...... 435/6.15; 435/6.1; 435/6.11; 435/6.12; 435/91.2; 536/23.1; 536/23.7; 536/24.32; 536/24.33

(58) Field of Classification Search .................. None
See application file for complete search history.

(56) References Cited

OTHER PUBLICATIONS

Wallach et al. European J Immunology. 2003.33: 708-719.*
Picken et al. J Invest Dermatology. 1998.110:211-214.*
Mitsuhashi et al. Journal of Laboratory Analysis. 1996.10: 285-293.*

* cited by examiner

*Primary Examiner* — Carla Myers
(74) *Attorney, Agent, or Firm* — Siu K. Lo, Esq.

(57) ABSTRACT

Disclosed are oligonucleotides useful in methods for determining whether a sample contains *Borrelia afzelii*, a spirochete which is a causative agent of Lyme disease in humans. These oligonucleotides, which have nucleotide sequences derived from a coding segment of the gene encoding the p24 gene for the outer surface protein of *Borrelia afzelii*, are useful as forward and reverse primers for a polymerase chain reaction using nucleic acids from a biological sample as templates, and as probes for detecting any resultant amplicon. Detection of an amplicon indicates the sample contains *Borrelia afzelii*. Real-time PCR and detection using florescence resonance energy transfer is disclosed.

2 Claims, 5 Drawing Sheets

FIGURE 1

```
  1   ATGAAAGGAA TAAGTATTTT ATCATTACTA TTATTGGCAT TTTCTTGCAA ACAATATGGT
 61   AGTGTTAAGG CACTCACAGA AATTGCTTCT GATTCTGGAG ATAATAATTC ACTTGTCGTT
121   AGTGATAATT TAGCGGCTAA AGAGCTGATT GCCGAAAAAG GCCTACTTT AACATCACAG
181   GAATCTGAAA GATTAGAGGC TTTAAAAACC TTTTTAAAAG ACGCAATGGG TGTTAATGGT
241   AAAACAGGCG ATACAAAAGC CGAGTACGAC AAATCTTATA AAGAATTTTT TGATTGGCTT
301   TCTAAGGATG TTAACAAACA AAAAGAGTTT GTAAGTTGTT TTAACAATAT TTGTGGCATT
```
            ─────── afzelii p24 F1 ──────▶
```
361   GTTACTAAAG CAGTAGATGC AAGCAAGCAA AGGTATAAGG G CAATCAACA ATCCTTAGGT
```
                                    afzelii p24 F2
                                ──────────────────▶
```
421   TTTAATGAAT ATGTTTGTTA TGATATTAAA ACCAGAACTG GAGATGATTT AAGTTTATTT
``` afzelii p24 Probe
```
                    ◀──────────────────                     ◀──────────
481   TTCCAAAAAG TAGCTGATGC ATTTGGTGCT GAAGAGTACA AA AAGAAA GA TGATGAGAGC
``` afzelii p24 R1                afzelii p24 R2
    ◀──────────────             ◀──────────────
```
541   AGTCAAAAGC CTGAGAAATG CAATGAAGAG ATTTTCAAAG TAATCAAAAG AGTGTTTACA
601   GAAAGTGATA GTAATAATGA ATTAAAAAAT TTAAAAAATC ATGGAAATAT CTAA
```

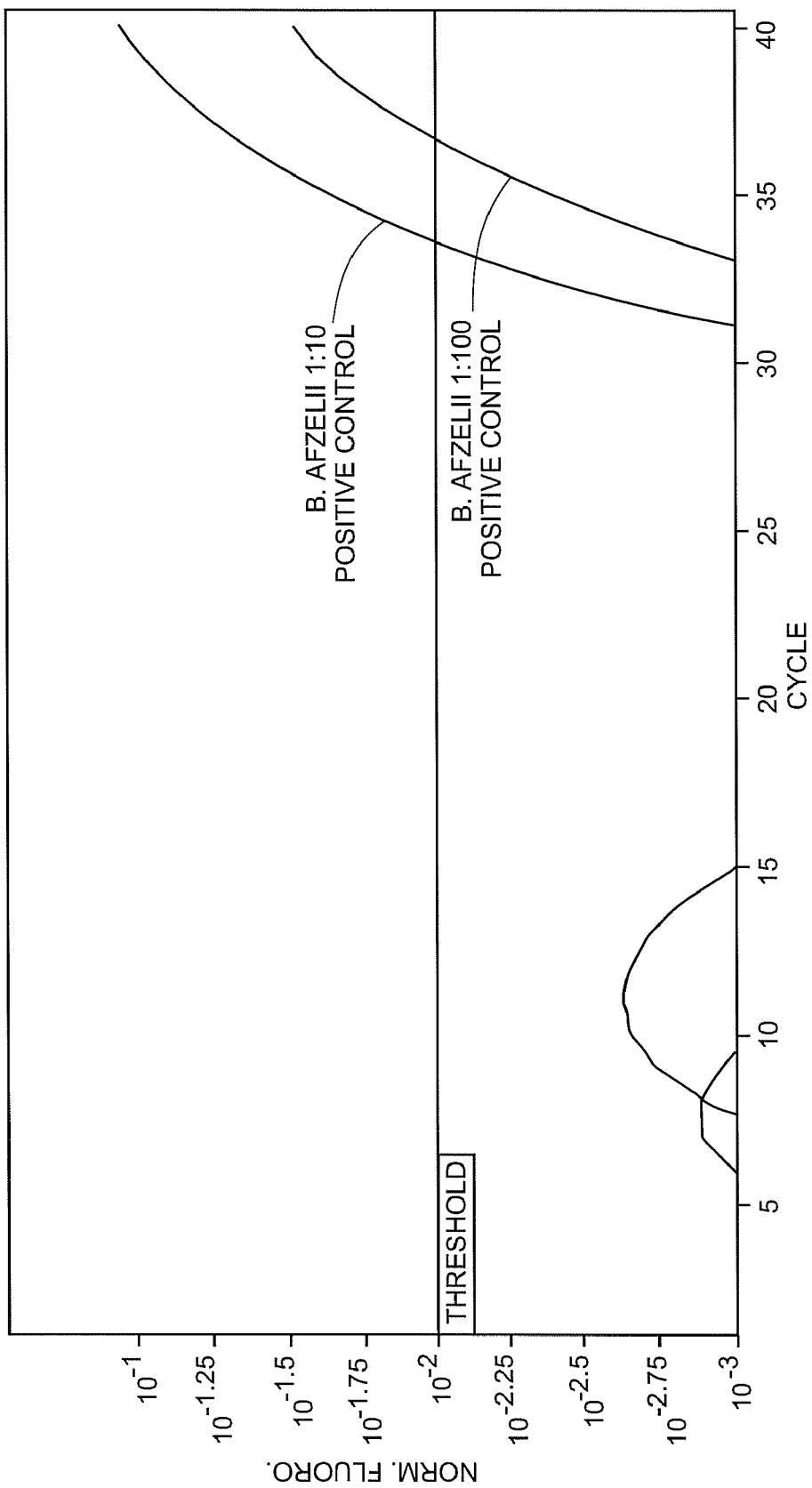

SEQUENCE LISTING

<160> NUMBER OF SEQ ID NOS: 17

<210> SEQ ID NO 1
<211> LENGTH: 654
<212> TYPE: DNA
<213> ORGANISM: Borrelia afzelii

<400> SEQUENCE: 1

| | | | | | | |
|---|---|---|---|---|---|---|
| atgaaaggaa | taagtatttt | atcattacta | ttattggcat | tttcttgcaa | acaatatggt | 60 |
| agtgttaagg | cactcacaga | aattgcttct | gattctggag | ataataattc | acttgtcgtt | 120 |
| agtgataatt | tagcggctaa | agagctgatt | gccgaaaaag | ggcctacttt | aacatcacag | 180 |
| gaatctgaaa | gattagaggc | tttaaaaacc | tttttaaaag | acgcaatggg | tgttaatggt | 240 |
| aaaacaggcg | atacaaaagc | cgagtacgac | aaatcttata | agaattttt | tgattggctt | 300 |
| tctaaggatg | ttaacaaaca | aaaagagttt | gtaagttgtt | ttaacaatat | ttgtggcatt | 360 |
| gttactaaag | cagtagatgc | aagcaagcaa | aggtataagg | gcaatcaaca | atccttaggt | 420 |
| tttaatgaat | atgtttgtta | tgatattaaa | accagaactg | gagatgattt | aagtttattt | 480 |
| ttccaaaaag | tagctgatgc | atttggtgct | gaagagtaca | aaaagaaaga | tgatgagagc | 540 |
| agtcaaaagc | ctgagaaatg | caatgaagag | attttcaaag | taatcaaaag | agtgtttaca | 600 |
| gaaagtgata | gtaataatga | attaaaaaat | ttaaaaaatc | atggaaatat | ctaa | 654 |

<210> SEQ ID NO 2
<211> LENGTH: 654
<212> TYPE: DNA
<213> ORGANISM: Borrelia afzelii

<400> SEQUENCE: 2

| | | | | | | |
|---|---|---|---|---|---|---|
| ttagatattt | ccatgatttt | ttaaattttt | taattcatta | ttactatcac | tttctgtaaa | 60 |
| cactcttttg | attactttga | aaatctcttc | attgcatttc | tcaggctttt | gactgctctc | 120 |
| atcatctttc | ttttgtact | cttcagcacc | aaatgcatca | gctacttttt | ggaaaaataa | 180 |
| acttaaatca | tctccagttc | tggttttaat | atcataacaa | acatattcat | taaaacctaa | 240 |
| ggattgttga | ttgcccttat | acctttgctt | gcttgcatct | actgctttag | taacaatgcc | 300 |
| acaaatattg | ttaaaacaac | ttacaaactc | ttttgtttg | ttaacatcct | tagaaagcca | 360 |
| atcaaaaaat | tctttataag | atttgtcgta | ctcggctttt | gtatcgcctg | ttttaccatt | 420 |
| aacacccatt | gcgtcttta | aaaggttttt | taaagcctct | aatctttcag | attcctgtga | 480 |
| tgttaaagta | ggccctttt | cggcaatcag | ctctttagcc | gctaaattat | cactaacgac | 540 |
| aagtgaatta | ttatctccag | aatcagaagc | aatttctgtg | agtgccttaa | cactaccata | 600 |
| ttgtttgcaa | gaaaatgcca | ataatagtaa | tgataaaata | cttattcctt | tcat | 654 |

<210> SEQ ID NO 3

```
<211> LENGTH: 23
<212> TYPE: DNA
<213> ORGANISM: Borrelia afzelii

<400> SEQUENCE: 3
gcaagcaagc aaaggtataa ggg                                          23

<210> SEQ ID NO 4
<211> LENGTH: 24
<212> TYPE: DNA
<213> ORGANISM: Borrelia afzelii

<400> SEQUENCE: 4
aggcttttga ctgctctcat catc                                         24

<210> SEQ ID NO 5
<211> LENGTH: 30
<212> TYPE: DNA
<213> ORGANISM: Borrelia afzelii

<400> SEQUENCE: 5
ttgtactctt cagcaccaaa tgcatcagct                                   30

<210> SEQ ID NO 6
<211> LENGTH: 30
<212> TYPE: DNA
<213> ORGANISM: Borrelia afzelii

<400> SEQUENCE: 6
agctgatgca tttggtgctg aagagtacaa                                   30

<210> SEQ ID NO 7
<211> LENGTH: 22
<212> TYPE: DNA
<213> ORGANISM: Borrelia afzelii

<400> SEQUENCE: 7
cagaactgga gatgatttaa gt                                           22

<210> SEQ ID NO 8
<211> LENGTH: 22
<212> TYPE: DNA
<213> ORGANISM: Borrelia afzelii

<400> SEQUENCE: 8
actttgaaaa tctcttcatt gc                                           22

<210> SEQ ID NO 9
<211> LENGTH: 14
<212> TYPE: DNA
<213> ORGANISM: Borrelia afzelii

<400> SEQUENCE: 9
caagcaagca aagg                                                    14

<210> SEQ ID NO 10
<211> LENGTH: 16
<212> TYPE: DNA
<213> ORGANISM: Borrelia afzelii

<400> SEQUENCE: 10
aggcttttga ctgctc                                                  16

<210> SEQ ID NO 11
```

```
<211> LENGTH: 18
<212> TYPE: DNA
<213> ORGANISM: Borrelia afzelii

<400> SEQUENCE: 11
agcaagcaaa ggtataag                                                      18

<210> SEQ ID NO 12
<211> LENGTH: 19
<212> TYPE: DNA
<213> ORGANISM: Borrelia afzelii

<400> SEQUENCE: 12
aggcttttga ctgctctca                                                     19

<210> SEQ ID NO 13
<211> LENGTH: 21
<212> TYPE: DNA
<213> ORGANISM: Borrelia afzelii

<400> SEQUENCE: 13
caagcaagca aaggtataag g                                                  21

<210> SEQ ID NO 14
<211> LENGTH: 22
<212> TYPE: DNA
<213> ORGANISM: Borrelia afzelii

<400> SEQUENCE: 14
aggcttttga ctgctctcat ca                                                 22

<210> SEQ ID NO 15
<211> LENGTH: 24
<212> TYPE: DNA
<213> ORGANISM: Borrelia afzelii

<400> SEQUENCE: 15
actcatgtga atgcggaaat caag                                               24

<210> SEQ ID NO 16
<211> LENGTH: 22
<212> TYPE: DNA
<213> ORGANISM: Borrelia afzelii

<400> SEQUENCE: 16
tgcaggttca agtcaattct tc                                                 22

<210> SEQ ID NO 17
<211> LENGTH: 30
<212> TYPE: DNA
<213> ORGANISM: Borrelia afzelii

<400> SEQUENCE: 17
tccatctcat aggccaatct attctccagg                                         30
```

COMPOSITIONS AND METHODS FOR DETECTING *BORRELIA AFZELII*

CROSS-REFERENCE TO RELATED APPLICATIONS

This application is a continuation of U.S. Ser. No. 12/156,029 filed May 29, 2008, which claims the benefit of priority to U.S. Provisional Application No. 60/932,642 filed Jun. 1, 2007, the entire disclosures of which are hereby incorporated by reference in their entirety.

FIELD

Example embodiments are generally directed to sensitive and specific PCR assays for detecting *Borrelia afzelii*. Example embodiments also provide forward and reverse primers to target against the p24 gene of an outer surface on *Borrelia afzelii*, as well as hybridization probes containing a fluorescent moiety, such as fluorescein, so as to render a real-time PCR assay to detect the presence of *Borrelia afzelii*. Other example embodiments may include assays employing traditional PCR to detect the presence of *Borrelia afzelii*.

BACKGROUND

Lyme disease is one of most prevalent vector-borne human diseases in the United States, Europe and Asia. According to the United States Centers for Disease Control, the rate of Lyme disease infection in the United States is about 7.9 cases for every 100,000 persons. In some areas, such as New England, the infection rate reaches as high as 31.6 cases for every 100,000 persons. The disease is transmitted by the *Ixodes ricinus* ticks, which carry the spirochete *Borrelia* species including *Borrelia burgdorferi* or *Borrelia afzelii*. Through the tick bites, the spirochetes eventually affect multiple organs of the body. Lyme disease is clinically manifested by dermatologic (e.g., erythema migrans), cardiac, neurologic (e.g., meningitis), rheumatologic and musculoskeletal (e.g., joint pain) abnormalities. Left untreated, infected patients may acquire chronic lyme borreliosis. It is estimated that 61% of patients with erythema migrans would eventually develop neurologic, articular or cardiac symptoms.

In spite of the great demand, early detection for Lyme disease remains elusive. There are only few commercial tests currently available. In addition, significant limitations exist in these diagnostic methods, which include bacterial cultures, serologic methods, and genetic detection via polymerase chain reaction (PCR). See, A. C. Steere, *N. Engl. J. Med.* 321, 568-596 (1989). For example, culturing of *Borrelia* species from clinical samples is proven to be time consuming and tedious. Serologic detection of Lyme disease by Western Blot analysis is unreliable. Cross-reactions with other spirochetes are seen in some tests. In Western Blot analysis, purified microbial proteins are separated by SDS-PAGE and followed by detection using Lyme-specific anti-sera. However, antigenic variations among patients can make the test unreliable. Appearance of IgG and IgM titers in patients after infection may fluctuate greatly (e.g., IgG peaks 3-12 months and IgM peaks 3-6 weeks). Different titer responses among patients may yield false negative results, drastically limiting the accuracy of the serologic method.

U.S. Pat. No. 6,087,097 discloses detection of *B. burgdorferi* using a PCR assay based on specific genomic/plasmid DNA sequences of OspA gene from *B. burgdorferi*. However, this PCR-based assay has gained only limited success, in part because of its lack of specificity. Because of this limitation, the PCR technique has not become a standardized routine diagnosis.

Because ticks (e.g., *I. persulcatus*) may carry multiple spirochete *Borrelia* species, including *B. afzelii* and *B. garinii*, either singly or simultaneously, a combination of microorganisms may simultaneously invade a human body through a single tick bite. There are three established sub-groups of *Borrelia* bacteria: (i) *Borrelia garinii* (European "sub-group") which causes neurological illnesses; (ii) *Borrelia afzelii* (European "sub-group") which causes Acrodermatis atrophicans chronic and (iii) *Borrelia burgdorferi* (American "sub-group") which causes especially Arthritis and rheumatic pains).

SUMMARY

There is a continuing need for a specific, rapid and sensitive PCR assay to detect the presence of Lyme-disease causing spirochete in a clinical sample from a patient. More specifically, there is a need for a highly specific PCR assay to distinguish *Borrelia afzelii* from other microorganisms (e.g., *B. garinii* or *B. burgdorferi*). Disclosed herein are oligonucleotide primers and hybridization probes for use in polymerase chain reaction ("PCR") methods, such as real-time PCR methods, for specifically detecting *Borrelia afzelii* in a patient. Also disclosed are sensitive and specific PCR assays for detecting *Borrelia afzelii*. Further disclosed are kits that include such oligonucleotide primers and/or hybridization probes.

Provided herein are isolated oligonucleotide primers having about 15-25 nucleotides in length, which are capable of annealing under PCR conditions (such as real-time PCR conditions) to a segment of the p24 gene of *Borrelia afzelii*. The segment of the p24 gene may for example have a consensus sequence that has at least a 99%, 95% or 90% identity to the following sequences: (a) nucleotides 379-401 of SEQ ID NO: 1, (b) nucleotides 453-474 of SEQ ID NO: 1, (c) nucleotides 103-126 of SEQ ID NO: 2, or (d) nucleotides 74-95 of SEQ ID NO: 2.

Example embodiments provide an isolated oligonucleotide primer consisting essentially of nucleotide sequence set forth in SEQ ID NO: 3, the nucleotide sequence set forth in SEQ ID NO: 4, the nucleotide sequence set forth in SEQ ID NO: 7, or the nucleotide sequence set forth in SEQ ID NO: 8. The term "consisting essentially of," throughout this application is intended to encompass sequences having at least 90%, 95% or 99% identity to those identified herein. Thus, the following embodiments are examples thereof.

Example embodiments provide an isolated oligonucleotide, which has at least about 99% identity to a nucleotide sequence of: (a) nucleotides 379-401 of SEQ ID NO: 1, (b) nucleotides 453-474 of SEQ ID NO: 1, (c) nucleotides 103-126 of SEQ ID NO: 2, or (d) nucleotides 74-95 of SEQ ID NO: 2.

Further example embodiments provide an isolated oligonucleotide, which has at least about 95% identity to a nucleotide sequence of: (a) nucleotides 379-401 of SEQ ID NO: 1, (b) nucleotides 453-474 of SEQ ID NO: 1, (c) nucleotides 103-126 of SEQ ID NO: 2, or (d) nucleotides 74-95 of SEQ ID NO: 2.

Further example embodiments provide an isolated oligonucleotide, which has at least about 90% identity to a nucleotide sequence of: (a) nucleotides 379-401 of SEQ ID NO: 1, (b) nucleotides 453-474 of SEQ ID NO: 1, (c) nucleotides 103-126 of SEQ ID NO: 2, or (d) nucleotides 74-95 of SEQ ID NO: 2.

Other example embodiments provide an isolated hybridization probe. The hybridization probe has a nucleotide sequence consisting essentially of a sequence complementary to consensus nucleotide sequence of nucleotides 492 through 521 of SEQ ID NO: 1 or nucleotides 134 through 163 of SEQ ID NO: 2. The hybridization probe may include a fluorescent reporter group, molecule or moiety, such as a fluorescein moiety, e.g., at its 5' or 3' end. According to example embodiments, the fluorescent moiety may be a 6-carboxy-fluorescein.

In example embodiments, the hybridization probe may have the nucleotide sequence set forth in SEQ ID NO: 5 or SEQ ID NO: 6.

According to example embodiments, the hybridization probe may have at least about 99%, 95% or 90% identity to a nucleotide sequence complementary to consensus nucleotide sequence of nucleotides 492 through 521 of SEQ ID NO: 1 or nucleotides 134 through 163 of SEQ ID NO: 2.

According to non-limiting example embodiments, provided are methods of detecting the presence of *Borrelia afzelii* in a biological sample. Such methods include:

(a) mixing (i) extracted DNA obtained from said biological sample, and (ii) a primer pair containing a forward primer and a reverse primer, which target p24 gene of *Borrelia afzelii*, (b) amplifying, in a PCR reaction, under conditions to allow production of an amplicon; and (c) detecting the presence or absence of *Borrelia afzelii*, in the sample.

According to further non-limiting example embodiments, methods are provided of detecting the presence of *Borrelia afzelii* in a biological sample using real-time PCR. Such methods include:

(a) mixing (i) extracted DNA obtained from the biological sample, (ii) a primer pair containing a forward primer and a reverse primer, that target p24 gene of *Borrelia afzelii*, and (iii) a hybridization probe that targets p24 gene of *Borrelia afzelii* in a PCR vessel, wherein the hybridization probe includes a fluorescent moiety;

(b) amplifying, in a real-time PCR reaction, under conditions to allow production of an amplicon; and (c) detecting the presence or absence of *Borrelia afzelii*, by detecting the presence or absence of a fluorescent signal resulting from the formation of the amplicon, wherein the presence of a fluorescent signal is indicative of the presence of *Borrelia afzelii*.

According to non-limiting example embodiments, the forward primer consists essentially of nucleotide sequence 379-401 set forth in SEQ ID NO.: 1 or nucleotide sequence 453-474 set forth in SEQ ID NO: 1, the reverse primer consists essentially of nucleotide sequence 103-126 set forth in SEQ ID NO: 2 or nucleotide sequence 74-95 set forth in SEQ ID NO: 2, and the hybridization probe consists essentially of nucleotide sequence 492-521 of SEQ ID NO: 1 or nucleotide sequence 134-163 of SEQ ID NO: 2.

According to further non-limiting example embodiments, the forward primer has at least 99%, 95% or 90% identity to a nucleotide sequence 379-401 set forth in SEQ ID NO: 1 or nucleotide sequence 453-474 set forth in SEQ ID NO: 1, the reverse primer has at least 90%, 95% or 99% identity to a nucleotide sequence 103-126 set forth in SEQ ID NO: 2 or nucleotide sequence 74-95 set forth in SEQ ID NO: 2, and the hybridization probe has at least 90%, 95% or 99% identity to a nucleotide sequence 492-521 of SEQ ID NO: 1 or nucleotide sequence 134-163 of SEQ ID NO: 2.

According to example embodiments, the forward primer consists essentially of a nucleotide sequence set forth in SEQ ID NO: 3, and a reverse primer consists essentially of a nucleotide sequence set forth in SEQ ID NO: 4. According to other example embodiments, the forward primer consists essentially of a nucleotide sequence set forth in SEQ ID NO: 7, and a reverse primer consists essentially of a nucleotide sequence set forth in SEQ ID NO: 8.

According to example embodiments, the fluorescent moiety may be a fluorescein, and more particularly, 6-carboxy-fluorescein, which may be attached at a 5'- or 3' end of the hybridization probe.

In other example embodiments kits are provided for PCR for detection of *Borrelia afzelii*. Example kits may include the following:

(a) a forward primer that anneals to a *Borrelia afzelii* consensus sequence consisting essentially of nucleotides 379-401 of SEQ ID NO: 1;

(b) a reverse primer that anneals to a *Borrelia afzelii* consensus sequence consisting essentially of nucleotides 103-126 of SEQ ID NO: 2; and (c) instructions for using said forward primer and reverse primer in performing PCR to detect a presence of *Borrelia afzelii* in a sample.

Other example kits may include the following:

(a) a forward primer that anneals to a *Borrelia afzelii* consensus sequence consisting essentially of nucleotides 453-474 of SEQ ID NO: 1;

(b) a reverse primer that anneals to a *Borrelia afzelii* consensus sequence consisting essentially of nucleotides 74-95 of SEQ ID NO: 2; and (c) instructions for using said forward primer and reverse primer in performing PCR to detect a presence of *Borrelia afzelii* in a sample.

Kits are also provided for real-time PCR in particular. According to such embodiments, the kits above may further include a hybridization probe having a nucleotide sequence consisting essentially of a sequence set forth in SEQ ID NO: 5 or SEQ ID NO: 6, wherein the probe includes a fluorescent moiety; and the instructions are instructions for using the forward primer, reverse primer and hybridization probe in performing real-time PCR in detecting a presence of *Borrelia afzelii* in a sample.

Thus, according to example embodiments, kits are provided for real-time PCR for detection of *Borrelia afzelii*, which include the following:

(a) a forward primer that anneals to a *Borrelia afzelii* consensus sequence consisting essentially of nucleotides 379-401 of SEQ ID NO: 1;

(b) a reverse primer that anneals to a *Borrelia afzelii* consensus sequence consisting essentially of nucleotides 103-126 of SEQ ID NO: 2;

(c) a hybridization probe having a nucleotide sequence consisting essentially of a sequence set forth in SEQ ID NO: 5 or SEQ ID NO: 6, wherein the probe has a fluorescent moiety; and (d) instructions for using the forward primer, reverse primer and hybridization probe in performing real-time PCR in detecting the presence of *Borrelia afzelii*.

In other example embodiments, kits are provided for real-time PCR for detection of *Borrelia afzelii*, which include:

(a) a forward primer that anneals to a *Borrelia afzelii* consensus sequence consisting essentially of nucleotides 453-474 of SEQ ID NO: 1;

(b) a reverse primer that anneals to a *Borrelia afzelii* consensus sequence consisting essentially of nucleotides 74-95 of SEQ ID NO: 2;

(c) a hybridization probe having a nucleotide sequence consisting essentially of a sequence set forth in SEQ ID NO: 5 or SEQ ID NO: 6, wherein the oligonucleotide probe has a fluorescent moiety; and (d) instructions for using the forward primer, reverse primer and hybridization probe in performing real-time PCR in detecting the presence of *Borrelia afzelii*.

BRIEF DESCRIPTION OF THE FIGURES

Embodiments of the invention are herein described, by way of non-limiting example, with reference to the following accompanying Figures:

FIG. 1 depicts the nucleotide sequence of the p24 gene (the plus strand) from *B. afzelii* (SEQ ID NO: 1). The sequence complementary to the primers (i.e., afzelii p24 F1 and afzelii p24 F2, afzelii p24 R1 and afzelii p24 R2) and hybridization probe (i.e., afzelii probe) used in PCR is bold-faced. The nucleotide sequence of p24 gene is available from GenBank Accession Number AJ430848.

FIG. 5 depicts real-time PCR amplification of *Borrelia afzelii* p24 gene using the primer set of SEQ ID NO: 13 (90% identity to afzelii p24 F1) and SEQ ID NO: 14 (90% identity to afzelii p24 R1).

DETAILED DESCRIPTION

Figure 2:
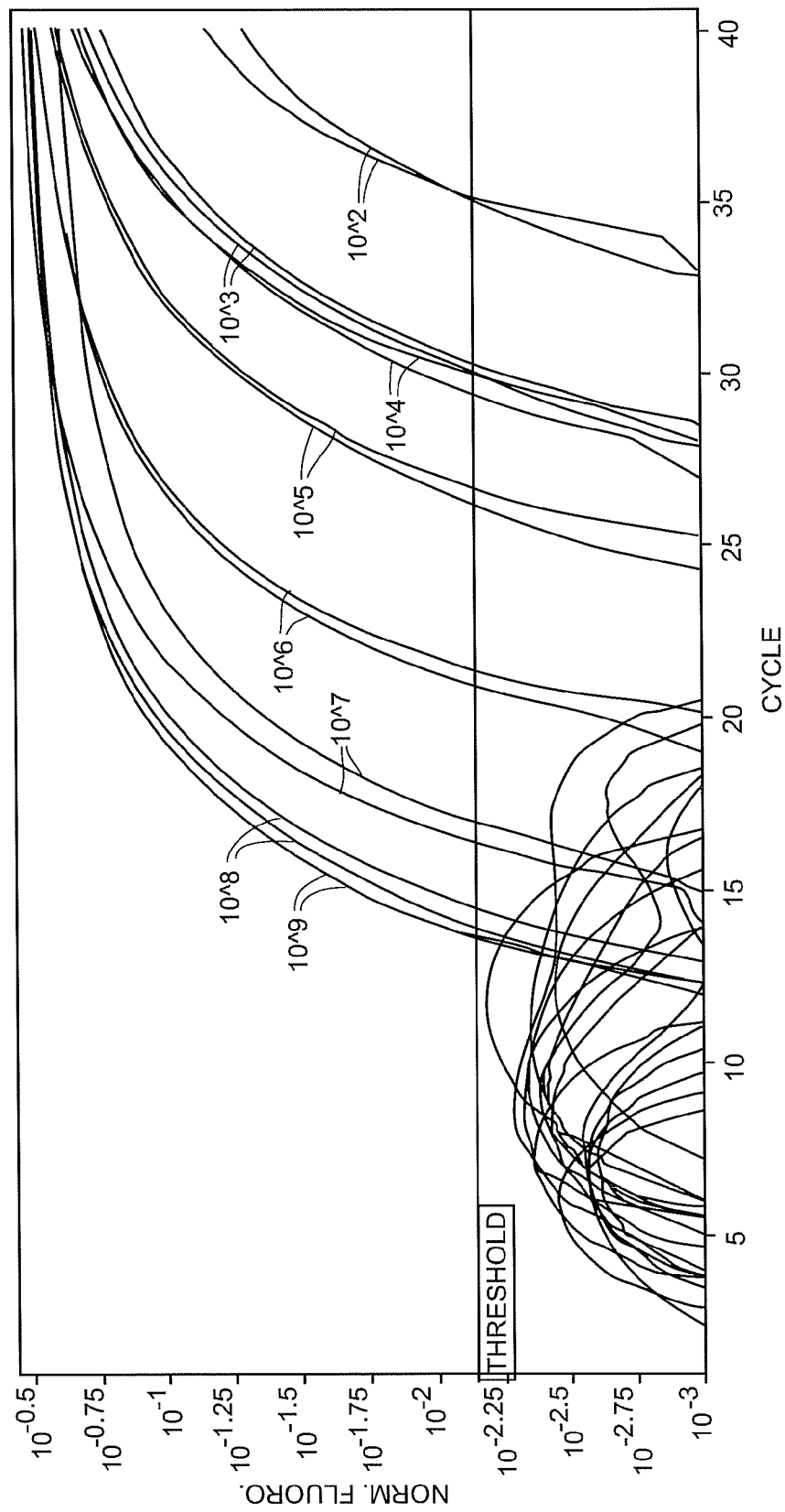
FIG. 2 depicts the linear range of detection of the *Borrelia afzelii* p24 gene by Real-Time PCR. The pafzeliiLN plasmid dilutions (in duplicate) are $1\times10^9$, $1\times10^8$, $1\times10^7$, $1\times10^6$, $1\times10^5$, $1\times10^4$, and $1\times10^3$ copies/reaction. Using 36 cycles, the real-time PCR assay is reproducibly detecting as well as 100 copies/reaction.

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

Provided herein are sensitive and specific methods using PCR, such as real-time PCR, to detect the presence of *Borrelia afzelii* in a biological sample. In accordance with example embodiments primers and probes are also provided, which may be used to detect *Borrelia afzelii*. Also provided are kits including such primers and/or probes. Embodiments of the present invention provide much-needed increased sensitivity of real-time PCR and are proven to have high specificity.

In describing example embodiments, specific terminology is employed for the sake of clarity. However, the embodiments are not intended to be limited to this specific terminology.

As used herein, "a" or "an" may mean one or more. As used herein, "another" may mean at least a second or more.

As used herein, an "isolated" oligonucleotide refers to an oligonucleotide that is synthesized chemically (not a naturally occurring nucleic acid).

As indicated above, the term "consisting essentially of," throughout this application is intended to encompass sequences having at least 99%, 95% or 90% identity to those identified herein.

As used herein, the term "biological sample" may include but are not limited to fluid or tissue samples such as blood (e.g., whole blood, blood serum, etc), bronchioalveolar lavage, nasal swabs, cerebrospinal fluid, urine, synovial fluid, brain and other neurological tissues, cardiac tissue, skin, lymph nodes, and the like from a mammal such as a human or domestic animal. Extraction of nucleic acids from biological samples is known to those of skill in the art.

Oligonucleotide Primers of the Invention

A. Oligonucleotide Primer Sets Target Against the p24 Gene of *Borrelia afzelii*

The present inventors discovered, inter alia, a PCR assay to detect specifically *Borrelia afzelii* by amplifying, for example, a portion of the p24 nucleic acid of the *Borrelia afzelii*. The p24 gene encodes an outer surface protein of *Borrelia afzelii*. The full length nucleotide sequence of the p24 gene in *Borrelia afzelii* is publicly available. (GenBank Access No. 22266317, the entire content of which is hereby incorporated by reference). The p24 gene contains two polynucleotide strands (i.e., a 5' to 3' "plus" strand and a 3' to 5' "minus" strand). The nucleotide sequence of SEQ ID NO: 1 represents the plus strand (See, FIG. 1). The nucleotide sequence of SEQ ID NO: 2 represents the minus (i.e., reverse complementary) strand of the nucleotide sequence of SEQ ID NO: 1.

In *Borrelia burgdorferi*, the OspA gene has been used in PCR detection for *Borrelia burgdorferi*. (See, U.S. Pat. No. 6,087,097). However, the PCR amplification of the OspA gene is not specific (i.e., the primers used to detect OspA in *Borrelia burgdorferi* also detect other *Borrelia* strains). Contrary to the methods using the OspA gene, the present inventors discovered that the p24 gene is highly specific for *Borrelia afzelii*.

Example embodiments herein are therefore drawn to isolated oligonucleotide primers and primer sets, which are capable of annealing under highly stringent hybridization conditions, including PCR conditions, and real-time PCR conditions, to a segment of the p24 gene of *Borrelia afzelii*. As used herein, a primer set contains a pair of primers; that is, a forward primer and a reverse primer. In an example embodiment, the primer set (i.e., forward primer and reverse primer) sufficiently anneals to the p24 gene segment during the PCR conditions; such as real-time PCR conditions.

Highly stringent hybridization conditions include the following conditions: 6×SSC and 65° C.; highly stringent hybridization conditions described in Ausubel et al., 2002, Short Protocols in Molecular Biology, 5th edition, Volumes 1 and 2, John Wiley & Sons, Inc., Hoboken, N.J., the entire contents of which are hereby incorporated by reference; and highly stringent hybridization conditions described in Ausubel et al., 1997, Short Protocols in Molecular Biology, 3rd edition, John Wiley & Sons, Inc., New York, N.Y., the entire contents of which are hereby incorporated by reference.

Example embodiments also relate to labeled nucleic acids that can act as probes (i.e., hybridization probes) to facilitate the detection of an amplification product of *B. afzelii*, using an isolated oligonucleotide primer set. According to example embodiments, when hybridized to the target gene (e.g., p24), the hybridization probe (which may carry a fluorescent moiety such as a fluorescein moiety on its 5' end and a quencher on its 3' end or a fluorescent moiety on its 3' end and a quencher on its 5' end), is degraded when there is successful amplification initiated by the forward primer and reverse primer against the target gene.

The design of specific primers and hybridization probes may be performed, for example, using a computer program such as Beacon Designer 4.02 (Build 402003) (PREMIER Biosoft International, Palo Alto, Calif.). Other equivalent computer programs such as OLIGO (Molecular Biology Insights, Inc., Cascade, Colo.) may also be used. One of ordinary skill in the art would appreciate the various factors in the primer design. The factors may include, but are not limited to, melting temperatures of the primer pairs, length of the primers or probes and size of the amplicon products. Embodiments of the present invention are not limited to the specific primers and hybridization probes explicitly provided herein. For example, other primers that amplify a p24 gene of *Borrelia afzelii* may be used in accordance with the present invention.

As used herein, the term "p24 primers" refers to oligonucleotide primers (i.e., a forward primer and a reverse primer) that anneal specifically to the p24 nucleic acid in *Borrelia afzelii* and thus initiate the amplifying process under PCR conditions. As used herein, the term "amplifying" refers to a process of synthesizing nucleic acid molecules that are complementary to both strands of a template nucleic acid molecule (e.g., p24 nucleic acid molecule). Amplifying during a PCR reaction typically involves several steps such as denaturing the template nucleic acid (at an elevated temperature), annealing primers to the template nucleic acid (at a temperature which is below the melting temperature of the primers), and elongating from the primers to produce an amplicon. It is to be understood that amplification typically requires the substrates (i.e., deoxyribonucleoside triphosphates) and a DNA polymerase enzyme (e.g., Taq DNA polymerase) as well as appropriate buffer and co-factors (e.g., magnesium chloride etc). The optimal concentrations of amplification substrates, enzyme and co-factors can conveniently be determined by one skilled in the art.

B. Forward Primers of the p24 Gene of *Borrelia afzelii*

In example embodiments, a plurality of forward primers is provided. Typically, oligonucleotide forward primers are 15-25 nucleotides in length. Primers useful in such embodiments may include e.g., an oligonucleotide primer capable of annealing within a portion of the p24 gene in *Borrelia afzelii*, and thus providing a point of initiation in nucleic acid synthesis in a PCR process. A forward primer typically is single-stranded, and is designed to anneal to either the plus strand or minus strand of the p24 gene.

In a first example embodiment, the nucleotide sequence of a forward primer (i.e., sequence consisting essentially of the sequence set forth in SEQ ID NO: 3) corresponds to the p24 gene segment of the plus strand which consists essentially of the nucleotides 379 through 401 of SEQ ID NO: 1 (See, FIG. 1). This particular forward primer is capable of annealing to the minus strand spanning the bases 254-276.

In a second example embodiment, the nucleotide sequence of another forward primer (i.e., sequence consisting essentially of the sequence set forth in SEQ ID NO: 7) corresponds to the p24 gene segment of the plus strand which consists essentially of the nucleotides 453 through 474 of SEQ ID NO: 1. (See, FIG. 1). This particular forward primer is capable of annealing to the minus strand spanning the bases 181-202.

Accordingly, the forward primers consist of the nucleotide sequence of SEQ ID NO: 3 or SEQ ID NO: 7.(as well as sequences having at least about 99%, 95%, or 90% identity thereto, as described further below).

C. Reverse Primers of the p24 Gene of *Borrelia afzelii*

In example embodiments, a plurality of reverse primers is provided. As with the forward primers, oligonucleotide reverse primers may be 15-25 nucleotides in length. Reverse primers useful in the present invention may include oligonucleotide reverse primers, in conjunction with the forward primers, which anneal to a different portion and on a different strand of the p24 gene in *Borrelia afzelii*, thus providing an appropriate amplicon product in PCR. Similar to the forward primers, the reverse primers may be single-stranded and can anneal to either the plus strand or minus strand of the p24 gene. When forward primer anneals to the plus strand, reverse primer anneals to the minus strand, and vice versa.

In a first example embodiment, the nucleotide sequence of a reverse primer (i.e., sequence consisting essentially of the sequence set forth in SEQ ID NO: 4) corresponds to the p24 gene segment of the minus strand which consists essentially of the nucleotides 103 through 126 of SEQ ID NO: 2 (See, FIG. 1). This particular reverse primer is capable of annealing to the plus strand spanning the bases 529-552.

In a second example embodiment, the nucleotide sequence of a reverse primer (i.e., sequence consisting essentially of the sequence set forth in SEQ ID NO: 8) corresponds to the p24 gene segment of the minus strand which consists essentially of the nucleotides 74 through 95 of SEQ ID NO: 2 (See, FIG. 1). This particular reverse primer is capable of annealing to the plus strand spanning the bases 560-580.

Thus, according to example embodiments, the reverse primers consist of the nucleotide sequence of SEQ ID NO: 4 or SEQ ID NO: 8, (as well as sequences having at least about 99%, 95%, or 90% identity thereto, as described further below).

Given what is disclosed herein, one of ordinary skill in the art would know how to design and prepare primer sets that are useful in amplifying a segment of the p24 gene in *Borrelia afzelii*. As indicated above, the primers and primer sets provided are merely exemplary.

D. Example Primer Sets

The primer sets are used in combination with PCR reagents under reaction conditions to initiate primer extension. A primer set useful in the present embodiments, may include a forward primer that anneals to one strand of the p24 gene, and a reverse primer that anneals to the opposing strand of the p24 gene. The location between the forward primers and reverse primers may be optimized with a computer program to yield an appropriate amplicon size.

In example embodiments, a first primer set is provided, which includes a forward primer having the nucleotide sequence as set forth in SEQ ID NO: 3 and a reverse primer having the nucleotide sequence as set forth in SEQ ID NO: 4.

In other example embodiments, a second primer set is provided, which includes a forward primer having the nucleotide sequence as set forth in SEQ ID NO: 7, and a reverse primer having the nucleotide sequence as set forth in SEQ ID NO: 8.

E. Polynucleotide Length of Primers

One of ordinary skill in the art would recognize the nucleotide length required for the primer set and would be able to conveniently determine the optimal length of the primers. In example embodiments, the primers have about 15-25 base-pairs (bp) in length. According to further example embodiments, the primers have about 22-24 by nucleotides.

F. Primers With High Percent Sequence Identity to Sufficiently Anneal During PCR It is understood that the nucleotide sequence of the primers that anneal to the p24 gene may somewhat vary without affecting its annealing ability in a PCR reaction. Thus, the present methods, primers, and kits are intended to encompass these slight variations.

In example embodiments, the forward primer is at least about 99% identical to the p24 gene segment corresponding to the nucleotide sequence set forth in SEQ ID NO: 3, or SEQ ID NO: 7. According to further examples, the forward primer has at least about 95% identity to SEQ ID NO: 3, or SEQ ID NO: 7. According to even further examples, the forward primer has at least about 90% identity to SEQ ID NO: 3, or SEQ ID NO: 7.

In other example embodiments, the reverse primer is at least about 99% identical to the p24 gene segment corresponding to the nucleotide sequence set forth in SEQ ID NO: 4, or SEQ ID NO: 8. According to further examples, the reverse primer has at least about 95% identity to SEQ ID NO: 4, or SEQ ID NO: 8. According to even further examples, the reverse primer has at least about 90% identity to SEQ ID NO: 4, or SEQ ID NO: 8.

Example embodiments further include isolated oligonucleotide primers, wherein the oligonucleotide primers have at least 99%, 95%, or 90% identity to a nucleotide sequence selected from the group consisting of (a) nucleotides 379-401 of SEQ ID NO: 1, (b) nucleotides 453-474 of SEQ ID NO: 1, (c) nucleotides 103-126 of SEQ ID NO: 2, and (d) nucleotides 74-95 of SEQ ID NO: 2.

Pairwise nucleotide sequence alignments and determination of percent identities may be performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153, the entire contents of which are hereby incorporated by reference. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80, the entire contents of which are hereby incorporated by reference. In other embodiments, the oligonucleotide and the segment of the polynucleotide include the same number of nucleotides.

Hybridization Probe of the p24 Gene of *Borrelia afzelii*

Example embodiments are also drawn to isolated oligonucleotide hybridization probes capable of hybridizing under highly stringent hybridization conditions to a segment of a polynucleotide directed to the p24 gene of *Borrelia* afzelii. In example embodiments, the hybridization probe may include a dual labeled hybridization probe or a molecular beacon.

As described further herein, example embodiments of PCR assays for detection *Borrelia afzelii* include conventional PCR assays and real-time PCR assays. Real-time PCR offers a much-increased sensitivity for detection, as compared to conventional PCR, making it an ideal assay. A PCR assay in conjunction with fluorescence resonance energy transfer (FRET) technique may be employed for real-time PCR. In such an assay, a donor fluorescent moiety and a corresponding acceptor fluorescent moiety are positioned in such a manner that the energy transfer taking place between two fluorescent moieties can be detected and monitored via a machine. It is understood that the emission spectrum of an acceptor fluorescent moiety overlaps with the excitation spectrum of a donor fluorescent moiety. One of ordinary skill in the art would know how to select a fluorescent donor moiety and its corresponding acceptor moiety in FRET.

According to non-limiting example embodiments, TAQMAN® technology may be used to detect the presence of an amplification product, i.e., to detect the presence or absence of *Borrelia afzelii* in a real time PCR assay. Typically, in FRET involving TAQMAN® technology to detect the presence of an amplification product, a hybridization probe is labeled with two fluorescent moieties. When a first fluorescent moiety is excited (e.g., light with specific wavelength), the absorbed energy is transferred to a second fluorescent moiety in accordance with the principle of FRET. When the second fluorescent moiety is a quencher molecule, the energy transferred is absorbed (i.e., quenched) and no detection of fluorescence emission can be detected. During the annealing step of a PCR reaction, a hybridization probe (dually labeled with two fluorescent moieties) is annealed to the p24 gene. If a successful amplification reaction occurs, the Taq polymerase then degrades (attributed by the 5' to 3' exonuclease activity) the hybridization probe. The degradation of hybridization probe by Taq polymerase allows the first fluorescent moiety to be spatially separated from the second fluorescent moiety; thus permitting the detection of fluorescence emission (as the quencher fails to absorb the transferred energy).

Typically, hybridization probes are about 20-35 base pairs in length, so as to sufficiently anneal to the target nucleic acid molecules (i.e., p24). The primers may contain e.g., 30 nucleotides. As used herein, "p24 hybridization probe" refers to oligonucleotide probe that anneals specifically to the p24 nucleic acid sequences and provide fluorescence signals during annealing of PCR polymerization.

In accordance with example embodiments, molecular beacon technology in conjunction with PCR may also be used. In this technology, a hybridization probe is also labeled with a first fluorescent moiety and a second fluorescent moiety. Like TAQMAN® technology, the second fluorescent moiety is generally a quencher. Typically, molecular beacon technology uses an oligonucleotide as a hybridization probe that permit hairpin formation (i.e., the hybridization probe contains nucleotide sequences to form a hairpin). As a result, the two fluorescent moieties present on the hybridization probe are in close proximity when in solution (due to hairpin formation). However, if there is a successful amplification and annealing, the hybridization probe anneals to the target nucleic acids and thus destroys the hairpin formation, separating the two florescent moieties and allowing the detection of the emission of fluorescent energy.

According to non-limiting example embodiments, an isolated hybridization probe is provided having a nucleotide sequence consisting essentially of a sequence complementary to consensus nucleotide sequence of nucleotides 492 through 521 of SEQ ID NO: 1 or nucleotides 134 through 163 of SEQ ID NO: 2, where the hybridization probe includes at least one fluorescent moiety. According to example embodiments, the hybridization probe anneals to the p24 gene segment consisting essentially of nucleotides 492 through 521 of SEQ ID NO: 1 (FIG. 1). In other example embodiments, the hybridization probe anneals to the p24 gene segment consisting essentially of nucleotides 134 through 163 of SEQ ID NO: 2. (FIG. 1).

According to example embodiments, the hybridization probe includes at least one fluorescent moiety (or molecule), such as a fluorescein moiety. The fluorescent moiety may be located e.g., at the 5' end of the hybridization probe. Examples of suitable fluorescent moieties that may be used in accordance with real-time PCR methods would be known to those skilled in the art. For example fluorescent reporter or fluorophore (e.g. 6-carboxy-fluorescein, acronym: FAM, or tetrachlorofluorescein, acronym: TET) may be covalently attached to the 5' end of the probe. According to non-limiting example embodiments, the fluorescent molecule is a 6-carboxy-fluorescein moiety attached to the 5' end of the hybridization probe.

In further example embodiments, the hybridization probe may include a quencher. The fluorescent molecule emits its emission light and is quenched by a quencher during a real-time PCR reaction. The quencher may be attached to the opposite end of the hybridization probe from the fluorescent moiety, e.g., to the 3' end of the hybridization probe. Example quenchers may include e.g., Black Hole Quencher 1, Black Hole Quencher 2, Iowa Black FQ, Iowa Black RQ-sp, and the like.

In example embodiments, the hybridization probe consists essentially of nucleotide sequence of SEQ ID NO: 5 or SEQ ID NO: 6, as well as at least one fluorescent moiety, and may further include a quencher.

It is understood that the nucleotide sequence of the isolated hybridization probe may also somewhat vary. The present methods, probes, and kits are intended to encompass these variations as well. In particular, according to example embodiments, hybridization probes may have at least 99%, 95% or 90% identity to a nucleotide sequence selected from the group consisting of SEQ ID NO: 5 or SEQ ID NO: 6. Example embodiments also provide an isolated hybridization probe, which has at least about 99%, 95% or 90% identity to a nucleotide sequence complementary to consensus nucleotide sequence of nucleotides 492 through 521 of SEQ ID NO: 1 or nucleotides 134 through 163 of SEQ ID NO: 2.

Oligonucleotide Combinations of the Invention

Other embodiments are directed to a composition (e.g., a reaction mixture or a kit) including a first isolated oligonucleotide (e.g., a forward primer) and a second isolated oligonucleotide (e.g., a reverse primer).

In example embodiments, the composition includes a first forward primer which corresponds to (e.g., includes or consists essentially of) the nucleotides 379 through 401 of SEQ ID NO: 1 (i.e., SEQ ID NO: 3), and a first reverse primer which corresponds to (e.g., includes or consists essentially of) the nucleotides 103 through 126 of SEQ ID NO: 2 (i.e., SEQ ID NO: 4). The forward primer of SEQ ID NO: 3 and reverse primer of SEQ ID NO: 4 are capable of annealing under PCR conditions to the p24 gene segment and produce an amplicon.

In other embodiments, the composition includes a second forward primer which corresponds to the nucleotides 453 through 474 of SEQ ID NO: 1. (i.e., SEQ ID NO: 7) and a second reverse primer which corresponds to the nucleotides 75 through 95 of SEQ ID NO: 2 (i.e., SEQ ID NO: 8). The forward primer of SEQ ID NO: 7 and reverse primer of SEQ ID NO: 8 are capable of annealing under PCR conditions to the p24 gene segment and produce an amplicon.

Example embodiments provide a sensitive and specific PCR assay to detect *Borrelia afzelii*. In example embodiments, hybridization probes are provided. The hybridization probe is capable of annealing to nucleotide sequences contained in SEQ ID NO: 1 or SEQ ID NO: 2. The hybridization probe may be about 20-35 nucleotides long. According to example embodiments, the hybridization probe is about 30 nucleotides long.

In example embodiments, the hybridization probe comprises the nucleotide sequence of SEQ ID NO: 5. In other embodiments, the hybridization probe comprises the nucleotide sequence of SEQ ID NO: 6.

Methods

The p24 gene can be used as a diagnostic tool for determining the presence of *B. afzelii* in biological samples obtained from mammals such as a human subject. Example embodiments pertains to methods for determining whether a sample (e.g., a biological sample such as whole blood) contains *Borrelia afzelii*, wherein the methods include the following: (a) mixing DNA extracted from a biological sample with a primer pair that targets a p24 gene of *Borrelia afzelii* (e.g., where the primer pair may be included in a composition) (b) amplifying, by a polymerase chain reaction, a segment of the nucleic acid (directed to the p24 gene in *Borrelia afzelii*) to produce an amplicon, wherein production of the amplicon is primed by the forward and reverse primers, and (c) detecting a presence or absence of *Borrelia afzelii* in the sample if the amplicon is detected. The forward primer may be capable of annealing under PCR conditions to a polynucleotide consisting of the nucleotide sequence of SEQ ID NO: 2, wherein the reverse primer is capable of annealing to a polynucleotide consisting of the nucleotide sequence of SEQ ID NO: 1. As part of the present methods, a vessel containing the primer pair and biological vessel may be may be incubated under conditions allowing production of the amplicon if the sample contains *Borrelia afzelii*.

In other example embodiments, the forward primer may be capable of hybridizing under PCR conditions to a segment of a polynucleotide, wherein the segment consists essentially of nucleotides 254 through 276 of SEQ ID NO: 2. In another embodiment, the reverse primer may be capable of hybridizing under the same conditions to a segment of a polynucleotide, wherein the segment consists essentially of nucleotides 529 through 552 of SEQ ID NO: 1.

In another embodiment, the forward primer is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the first polynucleotide consists of the nucleotide sequence of SEQ ID NO: 1. In another embodiment, the forward primer and the segment of the polynucleotide contain the same number of nucleotides. In another embodiment, the reverse primer is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the second polynucleotide consists of the nucleotide sequence of SEQ ID NO: 2. In another embodiment, the reverse primer and the segment of the second polynucleotide contain the same number of nucleotides.

In another embodiment, the forward primer is at least 90%, 91%, 92%, 93%, 94%, 95%, 96%, 97%, 98%, or 99% identical to, or is 100% identical to a segment of a polynucleotide, wherein the segment consists of the reverse complement of nucleotides 254 through 276 of SEQ ID NO:2 based on the Clustal V or W alignment method using the default parameters. In another embodiment, the reverse primer is at least 90%, 91%, 92%, 93%, 94%, 95%, 96%, 97%, 98%, or 99% identical to, or is 100% identical to a segment of a polynucleotide, wherein the segment consists of the reverse complement of nucleotides 529 through 552 of SEQ ID NO: 1 based on the Clustal V or W alignment method using the default parameters.

In another embodiment, the forward primer consists of a nucleotide sequence comprised by the nucleotide sequence of SEQ ID NO:1. In another embodiment the reverse primer consists of a nucleotide sequence comprised by the nucleotide sequence of SEQ ID NO:2. In another embodiment, the forward or forward primers comprise 15, 16, 17, 18, 19, 20, 21, 22, 23, 24, or 25 nucleotides. In another embodiment, the forward or reverse primers are 20-25 nucleotides long. In another embodiment, the forward primer includes a sequence consisting essentially of the nucleotide sequence of SEQ ID NO: 3. In another embodiment, the reverse primer includes a sequence consisting essentially of the nucleotide sequence of SEQ ID NO: 4.

Optionally, the mixing may include mixing a hybridization probe (e.g., a hybridization probe labeled with two fluorescent moieties in accordance with TAQMAN® technology or a molecular beacon) capable of detecting the amplicon if the amplicon is produced. In other embodiments, the oligonucleotide probe is capable of hybridizing under PCR conditions to a polynucleotide consisting of the nucleotide sequence of SEQ ID NO: 1 or SEQ ID NO: 2. In other embodiments, the oligonucleotide probe is capable of hybridizing under PCR conditions to a segment of a polynucleotide, wherein the segment consists essentially of nucleotides 134 through 163 of SEQ ID NO:2 or nucleotides 492 through 521 of SEQ ID NO:1.

In another embodiment, the hybridization probe is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the polynucleotide consists essentially of the nucleotide sequence of SEQ ID NO: 1 or SEQ ID NO: 2. In another embodiment, the oligonucleotide probe and the segment of the polynucleotide contain the same number of nucleotides.

In another embodiment, the oligonucleotide probe is at least 90%, 91%, 92%, 93%, 94%, 95%, 96%, 97%, 98%, or 99% identical to, or is 100% identical to a segment of a polynucleotide, wherein the segment consists essentially of the reverse complement of nucleotides 134 through 163 of SEQ ID NO:2 or nucleotides 492 through 521 of SEQ ID NO: 1 based on the Clustal V or W alignment method using the default parameters.

In other example embodiments, the oligonucleotide probe includes a nucleotide sequence comprised by the nucleotide sequence of SEQ ID NO: 1 or SEQ ID NO: 2. In another embodiment, the hybridization probe comprises 20, 21, 22, 23, 24, 25, 26, 27, 28, 29, 30, 31, 32, 33, 34, or 35 nucleotides. In another embodiment, the oligonucleotide probe is 30 nucleotides long. In another embodiment, the oligonucleotide probe consists essentially of the nucleotide sequence of SEQ ID NO: 5.

In other example embodiments, a 6-carboxy-fluorescein moiety is attached to the 5' end of the oligonucleotide probe. In another embodiment, a Black Hole Quencher 1 moiety is attached to the 3' end of the oligonucleotide probe. In other embodiments, the amplicon is detected by the oligonucleotide probe during real-time PCR. If convenient PCR is used, the formation amplicon is detected by gel electrophoresis after the PCR is completed.

Non-limiting example embodiments include methods of detecting presence of *Borrelia afzelii* in a biological sample, that include:

(a) mixing
 (i) DNA extracted from the biological sample,
 (ii) a primer pair comprising a forward primer and a reverse primer that target a p24 gene of *Borrelia afzelii*, and
 (iii) a hybridization probe, in a PCR vessel, wherein the hybridization probe comprises a fluorescent moiety;
(b) amplifying, in a real-time PCR reaction, under conditions to allow production of an amplicon; and
(c) detecting a presence or absence of *Borrelia afzelii*, by detecting a presence or absence of a fluorescent signal resulting from the formation of the amplicon, wherein the presence of a fluorescent signal is indicative of the presence of *Borrelia afzelii*.

The primers, probes, fluorescent moieties and other aspects of these and other embodiments may be as described herein throughout.

PCR Detection Assay

Example embodiments provide utilizing amplification approaches to quickly determine the presence of a particular gene. For purposes of this application, "amplifying" refers to a process of synthesizing nucleic acid molecules that are complementary to one or both strands of a template nucleic acid. With respect to *Borrelia afzelii*, the present inventors discovered amplifying the p24 gene to be a highly sensitive and specific approach to determine the presence of such microorganism. One of ordinary skill in the art would appreciate that amplifying a nucleic acid molecule typically includes (i) denaturing the template nucleic acid, (ii) annealing primers to the template nucleic acid at a temperature that is below the melting temperatures of the primers, and (iii) enzymatically elongating from the primers to generate an amplification product. Although the denaturing, annealing and elongating steps can be performed once, they are generally performed multiple times. As the amount of amplification product increases (often times exponentially), it increases the sensitivity of the assay. Typically, amplification requires the presence of a Taq DNA polymerase, an appropriate buffer and appropriate salts such as magnesium chloride or potassium chloride.

In example embodiments a real-time PCR assay is provided. The real-time PCR assay is more sensitive than a conventional PCR assay, (but conventional PCR assays may be alternatively utilized herewith). Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displaced in a graphical format through software developed for real-time analysis.

In addition to the forward primer and reverse primer (directed to the gene of interest—p24 gene), a single-stranded hybridization probe is also used. The hybridization probe may be a short oligonucleotide, usually 20-35 by in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 by long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein for detecting p24 gene in *Borrelia* afzelii. Further information on PCR amplification and detection using a Rotor-Gene can conveniently be found on Corbett's website.

In alternative embodiments, suitable hybridization probes such as intercalating dye (e.g., Sybr-Green I) or molecular beacon probes can be used. Intercalating dyes can bind to the minor grove of DNA and yield fluorescence upon binding to double-strand DNA. Molecular beacon probes are based on a hairpin structure design with a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The range of the primer concentration can optimally be determined. The optimization involves performing a dilution series of the primer with a fixed amount of DNA template. The primer concentration may be between about 50 nM to 300 nM. An optimal primer concentration for a given reaction with a DNA template should result in a low Ct-(threshold concentration) value with a high increase in fluorescence (5 to 50 times) while the reaction without DNA template should give a high Ct-value.

Real-time PCR methods include performing at least one cycling step that includes amplifying and hybridizing. An amplification step includes contacting the biological sample (suspected of containing DNA of *Borrelia afzelii*) with a pair of p24-primers to produce a p24 amplification product if a p24 nucleic acid molecule is present in the biological sample. The forward and reverse primers anneal to a target within or adjacent to a p24 nucleic acid molecule such that at least a portion of the amplification product contains nucleic acid sequence corresponding to p24 and, more importantly, such that the amplification product contains the nucleic acid sequences that are complementary to p24 probes. A hybridizing step also includes contacting the biological sample with a hybridization probe. The hybridization probe is complementary to either the 5' strand or 3' strand of the p24 gene. According to example embodiments, the hybridization probe anneals to the p24. When the p24 primers begin to anneal, the Taq polymerase breaks the hybridization probe and release donor fluorescent moiety as well as a corresponding acceptor fluorescent moiety. The method further includes detecting the presence or absence of FRET between the donor fluorescent moiety of the hybridization probe and the corresponding acceptor fluorescent moiety of the hybridization probe. Multiple cycling steps can be performed, e.g., in a thermocycler. The above-described methods for detecting p24 gene in a biological sample using primers and probes directed toward p24 gene also can be performed using other p24 gene-specific primers and probes.

Within each thermocycler run, control samples can be cycled as well. Positive control samples can also amplify, for example, a plasmid construct containing *Borrelia afzelii* p24 nucleic acid molecules. Such a plasmid control can be amplified internally (e.g., within each biological sample) or in separate samples run side-by-side with the patients' samples. Each thermocycler run also should include a negative control that, for example, lacks *Borrelia afzelii* p24 template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

Real-Time PCR Detection Kit for *Borrelia afzelii*

Example embodiments provide kits of manufacture, which may be used to detect specifically *Borrelia afzelii*. An article of manufacture (i.e., kit) according to the present invention includes a set of primers (i.e., a forward primer and a reverse primer) (directed to p24 gene) and optionally a hybridization probe (directed to p24 gene) used to detect *Borrelia afzelii*, contained within a suitable packaging material. Representative primers and hybridization probes provided in the kit for detection of *Borrelia afzelii* can be complementary to p24 gene encoding an outer surface membrane protein for *Borrelia afzelii*.

In embodiments including a hybridization probe, the hybridization probe may be conveniently labeled with a fluorescent moiety e.g., at its 5'-end and a quencher moiety at its 3'-end. Examples of suitable FRET donor fluorescent moieties and acceptor fluorescent moieties are provided herein. Alternatively, the hybridization probes supplied with the kit can be labeled. For example, an article of manufacture may include an instruction to tag the hybridization probe with a donor fluorescent moiety at its 5'-end and a corresponding acceptor fluorescent moiety at its 3'-end.

Methods of designing primers and hybridization probes are disclosed herein, and representative examples of primers and hybridization probes that amplify and hybridize to p24 nucleic acids encoding a p24 protein are provided.

Articles of manufacture or kits provided herein may also include instructions, such as a package insert having instructions thereon, for using the primers to detect of the presence of *Borrelia afzelii* in a biological sample. Such instructions may be for using the primer pairs and/or the hybridization probes to specifically detect *Borrelia afzelii* in a biological sample.

Non-limiting example embodiments may include kits for PCR detection of *Borrelia afzelii*, which include the following:

(a) a forward primer that anneals to a *Borrelia afzelii* consensus sequence consisting essentially of nucleotides 379-401 of SEQ ID NO: 1;

(b) a reverse primer that anneals to a *Borrelia afzelii* consensus sequence consisting essentially of nucleotides 103-126 of SEQ ID NO: 2; and (c) instructions for using the forward primer and reverse primer in performing PCR to detect a presence of *Borrelia afzelii* in a sample.

Other non-limiting example embodiments may include kits for PCR detection of *Borrelia afzelii*, which include:

(a) a forward primer that anneals to a *Borrelia afzelii* consensus sequence consisting essentially of nucleotides 453-474 of SEQ ID NO: 1;

(b) a reverse primer that anneals to a *Borrelia afzelii* consensus sequence consisting essentially of nucleotides 74-95 of SEQ ID NO: 2; and (c) instructions for using the forward primer and reverse primer in performing PCR to detect a presence of *Borrelia afzelii* in a sample.

According to non-limiting example embodiments, the kits may further include at least one hybridization probe having a nucleotide sequence consisting essentially of a sequence set forth in SEQ ID NO: 5 or SEQ ID NO: 6, wherein the probe includes at least one fluorescent moiety; and the instructions may include instructions for using the forward primer, reverse primer and hybridization probe in performing real-time PCR in detecting a presence of *Borrelia afzelii* in a sample.

Articles of manufacture and kits provided herein may additionally include reagents for carrying out the methods disclosed herein (e.g., buffers, Taq polymerase enzymes, cofactors, and agents to prevent contamination). Such reagents may be specific for one of the commercially available instruments described herein.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

PCR Conditions for the Testing of Clinical Samples (a) Nucleotide Sequences for the Primers and Hybridization Probes Nucleotide sequences of primer sets and hybridization probes were determined from the nucleotide sequences of SEQ ID NO: 1 and SEQ ID NO: 2, using computer programs of Beacon Designer 4.02 (Build 402003) (PREMIER Biosoft International, Palo Alto, Calif.). Primer sets and hybridization probes having the specified nucleotide sequences were purchased from Integrated DNA Technologies (Stokie, Ill.). The first primer set includes the first forward primer (afzelii p24 F1), and the first reverse primer (afzelii p24 R1) (See, details in FIG. 1).

(b) PCR Conditions

For the testing of clinical samples, each PCR was conducted in a volume of 25 µl containing the following: DNA extracted from a clinical sample (e.g., 500 ng), 600 nM of a first primer, which has the nucleotide sequence set forth in SEQ ID NO:3 ("the afzelii p24 F primer"), 600 nM of a second primer, which has the nucleotide sequence set forth in SEQ ID NO: 4 ("the afzelii p24 R primer"), 200 nM of a hybridization probe, which has the nucleotide sequence set forth in SEQ ID NO: 5, and 1×MDL Custom qPCR SuperMix (Quanta BioSciences, Inc., Gaithersburg, Md.). The hybridization probe ("the afzelii p24 probe") has a 6-carboxy-fluorescein moiety and a Black Hole Quencher 1 moiety attached to its 5'-end and 3'-end, respectively. 1×MDL Custom qPCR SuperMix has a Quanta BioSciences catalog number of 172-5008, and the 2× stock solution of the SuperMix contained 50 U/ml of AccuStart™ Taq DNA polymerase, 40 mM Tris-HCl (pH 8.4), 100 mM KCl, 6 mM $MgCl_2$, 400 nM dATP, 400 nM dCTP, 400 nM dGTP, 800 nM dUTP, 40 U/ml of UNG, and proprietary stabilizers of Quanta BioSciences, Inc. The afzelii p24 probe was present in the reaction mixture to monitor real-time synthesis of the amplicon resulting from each successful PCR. The afzelii p24 F primer, the afzelii p24 R primer, and the afzelii p24 probe were used at 600 nM and 200 nM, respectively.

(c) Real-Time PCR

Real-Time PCR was conducted using the Rotor-Gene 3000 platform (Corbett Research, Sydney, Australia). Parameters for each PCR were as follows: an initial incubation at 50° C. for 2 minutes to activate UNG, followed by incubation at 94° C. for 3 minutes to initially denature the DNA, inactivate the UNG, and activate the AccuStart™ Taq DNA polymerase. Next, 40 cycles of denaturation (94° C. for 20 seconds), and an annealing and extension (57° C. for 45 seconds) were performed with fluorescence acquisition (excitation at 470 nM and emission at 510 nM) immediately following each annealing and extension step. Fluorescence curves were analyzed with dynamic-tube normalization, slope correction, and automatic threshold determination by a best-fit line of three concentrations of the positive-control standard DNA using Corbett Robotics Rotor Gene software version 6.0.31 (Corbett Research, Sydney, Australia). The three concentrations of the positive-control standard DNA were $1×10^3$, $1×10^5$, and $1×10^7$ copies per reaction of pafzeliiLN (a plasmid which is described in Example 2). Negative template control (NTC) refers to plasmid lacking a template DNA and NTC threshold was set to a maximum 10%. The amplification target for *Borrelia afzelii* is p24, and successful amplification would result in a 173 by amplicon product.

Example 2

Positive-Control Standard DNA for the PCR

A positive-control standard DNA for the PCR used was prepared from *Borrelia afzelii* (commercially available, ATCC® No. 51567). PCR amplification was conducted using 200 ng of DNA extracted *Borrelia afzelii*. Parameters for this PCR were as follows: an initial incubation at 94° C. for 3 minutes, followed by 40 cycles of incubation at 94° C. for 1 minute, 57° C. for 1 minute, and 72° C. for 2 minutes, followed by a final incubation at 72° C. for 10 minutes. All other conditions for this reaction were similar to those described in Example 1. The resulting amplicon was cloned into the pCR®2.1-TOPO® vector (Invitrogen, Carlsbad, Calif.) to produce pafzeliiLN, which was used as the positive-control standard DNA.

Different dilutions of pafzeliiLN plasmid were prepared and the range of dilution includes $1×10^9$, $1×10^8$, $1×10^7$, $1×10^6$, $1×10^5$, $1×10^4$, and $1×10^3$ copies/dilution. The pafzeliiLN dilutions were run in a real-time PCR. As shown in FIG. 2, real-time PCR detects fluorescence at a range of concentrations ranging from $1×10^9$ to $1×10^2$ copies/dilutions, indicating that the primer set and PCR conditions are optimal in detecting *Borrelia afzelii*. After 36 PCR cycles, the assay reproducibly detects as few as 100 copies/reaction. (See, FIG. 2). The data indicate this real-time PCR in the detection of *Borrelia afzelii* is highly sensitive.

Example 3

Specificity of the PCR Using Primers Directed to the p24 Gene in *Borrelia afzelii*

Figure 3:
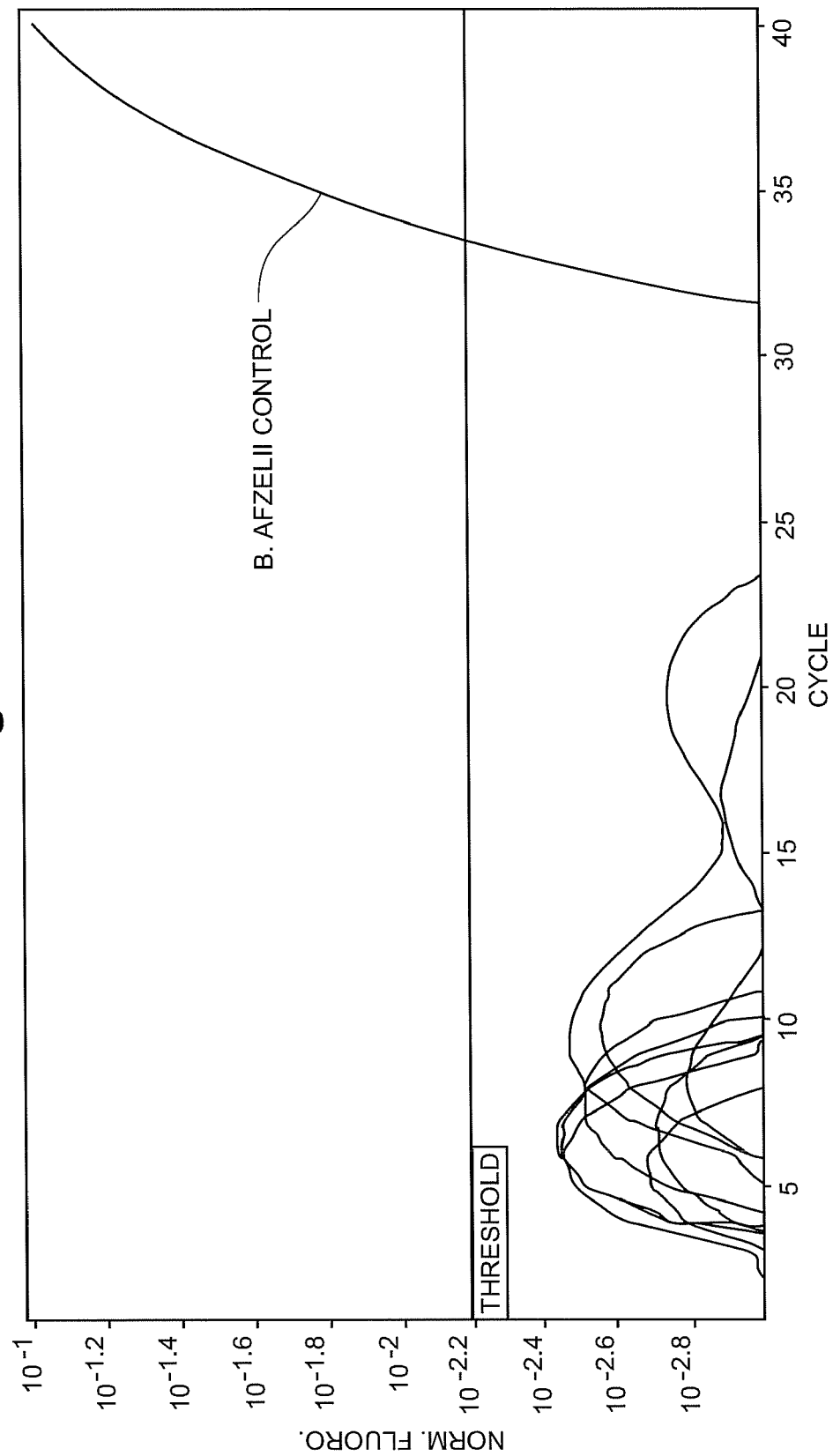
FIG. 3 depicts the *Borrelia afzelii* cross-reactivity analysis of the *Borrelia afzelii* p24 gene Real-Time PCR. Quantitation data displays the neat dilution of the *Borrelia afzelii* ATCC positive control. No amplification is shown in the eight cocktails tested and the content of each pathogen cocktail is available in Table 1.

The specificity of the PCR utilizing the combination of the afzelii p24 F primer, the afzelii p24 R primer, and the afzelii p24 probe was assessed by attempting to conduct real-time PCRs in cocktail format. As shown in FIG. 3, real-time PCR detects positive reactivity towards *B. afzelii*. We next tested all the forty-eight (48) species listed in the 10 cocktails. Duplicate reaction mixtures were tested and each reaction mixture contained DNA extracted from four or five types of pathogen summarized in Table 1. Each pathogen was purchased from ATCC®, except for *Candida lusitaneae* which was purchased from MicroBioLogics Inc. (Saint Cloud, Minn.).

TABLE 1

| | Number |
|---|---|
| Cocktail 1 | |
| Gardnerella vaginalis | ATCC ® No. 14018 |
| Neisseria gonorrhoeae | ATCC ® No. 27628 |
| Trichomonas vaginalis | ATCC ® No. 30246 |
| Ureaplasma urealyticum | ATCC ® No. 27618 |
| Chlamydia trachomatis | ATCC ® No. VR-901B |
| Cocktail 2 | |
| Bacteroides fragilis | ATCC ® No. 23745 |
| Mobiluncus curtisii | ATCC ® No. 35241 |
| Mobiluncus mulieris | ATCC ® No. 35243 |
| HTLV-I | ATCC ® No. CRL-8294 |
| Human herpesvirus 6B | ATCC ® No. VR-1467 |
| Cocktail 3 | |
| Herpes simplex virus 1 | ATCC ® No. VR-539 |
| Herpes simplex virus 2 | ATCC ® No. VR-734 |
| Human Papillomavirus | ATCC ® No. CRL-1550 |
| Epstein-Barr virus | ATCC ® No. CCL-86 |
| Cytomegalovirus | ATCC ® No. VR-807 |
| Cocktail 4 | |
| Candida albicans | ATCC ® No. 11651 |
| Candida glabrata | ATCC ® No. 2001 |
| Candida parapsilosis | ATCC ® No. 22019 |
| Candida tropicalis | ATCC ® No. 13803 |
| Aspergillus fumigatus | ATCC ® No. 14110 |
| Cocktail 5 | |
| Mycoplasma fermentans | ATCC ® No. 15474 |
| Mycoplasma pneumoniae | ATCC ® No. 15377 |
| Mycoplasma genitalium | ATCC ® No. 33530 |
| Mycoplasma penetrans | ATCC ® No. 55252 |
| Mycoplasma hominis | ATCC ® No. 14027 |
| Cocktail 6 | |
| Human herpesvirus-8 | ATCC ® No. CRL-2230 |
| Adenovirus type 1 | ATCC ® No. VR-1 |
| Coxsackievirus | ATCC ® No. VR-184 |
| Cryptococcus neoformans | ATCC ® No. 2344 |
| Babesia microti | ATCC ® No. 30222 |
| Cocktail 7 | |
| Chlamydia pneumoniae | ATCC ® No. VR-1356 |
| Helicobacter pylori | ATCC ® No. 43579 |
| Brucella ovis | ATCC ® No. 25840 |
| Borrelia burgdorferi | ATCC ® No. 35210 |
| Canine herpesvirus | ATCC ® No. VR-552 |
| Cocktail 8 | |
| Bartonella henselae | ATCC ® No. 49882 |
| Bartonella bacilliformis | ATCC ® No. 35686 |
| Bartonella Quintana | ATCC ® No. 51694 |
| Trichosporon cutaneum | ATCC ® No. 4151 |
| Cocktail 9 | |
| Influenza virus A | ATCC ® No. VR-1520 |
| Haemophilus parainfluenzae | ATCC ® No. 7901 |
| Human rhinovirus 6 | ATCC ® No. VR-1116AS/GP |
| Human rhinovirus 11 | ATCC ® No. VR-1121 |
| Adenovirus type 10 | ATCC ® No. VR-11 |
| Cocktail 10 | |
| Candida krusei | ATCC ® No. 14243 |
| Candida lusitaniae | MicroBioLogics No. 0774P |
| Candida dubliniensis | ATCC ® No. MYA-179 |
| Candida utilis | ATCC ® No. 9226 |

FIG. 3 depicts an exemplary quantitation data display in real-time PCR. No amplification is seen in the eight cocktails tested (i.e., cocktails 1-8) (below Ct threshold; in FIG. 3). The contents of each pathogen cocktail are listed in Table 1. Further shown in the following Table 2, no PCR amplification was observed in any of the cocktails tested (i.e., cocktails 1-10). In this series of studies, two samples were run separately. Neither of the two reaction mixtures containing DNA from Cocktails 1 through 10 was positive when using the combination of the afzelii p24 F primer, afzelii p24 R primer and the afzelii p24 probe (see Table 2). These data support that the primer probes and hybridization probe provide a high degree of specificity and accurate detection of *Borrelia afzelii*. No false positives were observed, among the 48 organisms tested.

TABLE 2

| Samples | Results |
|---|---|
| Cocktail 1 - Sample 1 | −* |
| Cocktail 1 - Sample 2 | − |
| Cocktail 2 - Sample 1 | − |
| Cocktail 2 - Sample 2 | − |
| Cocktail 3 - Sample 1 | − |
| Cocktail 3 - Sample 2 | − |
| Cocktail 4 - Sample 1 | − |
| Cocktail 4 - Sample 2 | − |
| Cocktail 5 - Sample 1 | − |
| Cocktail 5 - Sample 2 | − |
| Cocktail 6 - Sample 1 | − |
| Cocktail 6 - Sample 2 | − |
| Cocktail 7 - Sample 1 | − |
| Cocktail 7 - Sample 2 | − |
| Cocktail 8 - Sample 1 | − |
| Cocktail 8 - Sample 2 | − |
| Cocktail 9 - Sample 1 | − |
| Cocktail 9 - Sample 2 | − |
| Cocktail 10 - Sample 1 | − |
| Cocktail 10 - Sample 2 | − |
| Negative Control (no template DNA) | − |
| Positive Control (genomic DNA purified from *Borrelia afzelii* ATCC ® No. 51567) | +** |

*− indicates the absence of PCR amplification in the sample.
**+ indicates the presence of PCR amplification in the sample.

Example 4

Precision of the PCR Using Primers Directed to the p24 Gene in *Borrelia afzelii*

To determine the precision of the PCR when using primers directed specifically to the p24 gene in *Borrelia afzelii*, five (5) technicians were asked to independently conduct the real-time PCR. The study was performed in double-blinded manner, that is, none of the technicians knew the identity of the template DNA in the reaction mixture before and while they were conducting the PCRs. Each of five (5) technicians separately assessed the precision of the PCR utilizing the combination of the afzelii p24 F primer, the afzelii p24 R primer, and the afzelii p24 probe by conducting real-time PCRs using DNA obtained from nine (9) whole-blood clinical specimens. Each of the nine (9) reaction mixtures was known to be free of DNA of *Borrelia afzelii*. Then, in each of these nine (9) reaction mixtures, varying amount of DNA of *Borrelia afzelii* (i.e., pafzeliiLN) was spiked into these samples (i.e., samples 10-18). As summarized in Table 3, all five (5) technicians correctly determined which of the eighteen (18) reaction mixtures contained DNA of *Borrelia afzelii*, indicating that the PCR assay has high specificity. The high specificity is attributed to the specific forward/reverse primers and hybridization probe used.

TABLE 3

|  | | Technician | | | | |
| --- | --- | --- | --- | --- | --- | --- |
| Samples | Expected | A | B | C | D | E |
| 1 | –* | – | – | – | – | – |
| 2 | – | – | – | – | – | – |
| 3 | – | – | – | – | – | – |
| 4 | – | – | – | – | – | – |
| 5 | – | – | – | – | – | – |
| 6 | – | – | – | – | – | – |
| 7 | – | – | – | – | – | – |
| 8 | – | – | – | – | – | – |
| 9 | – | – | – | – | – | – |
| 10 ($1 \times 10^8$ copies of pafzeliiLN) | +** | + | + | + | + | + |
| 11 ($1 \times 10^7$ copies of pafzeliiLN) | + | + | + | + | + | + |
| 12 ($1 \times 10^7$ copies of pafzeliiLN) | + | + | + | + | + | + |
| 13 ($1 \times 10^6$ copies of pafzeliiLN) | + | + | + | + | + | + |
| 14 ($1 \times 10^6$ copies of pafzeliiLN) | + | + | + | + | + | + |
| 15 ($1 \times 10^5$ copies of pafzeliiLN) | + | + | + | + | + | + |
| 16 ($1 \times 10^5$ copies of pafzeliiLN) | + | + | + | + | + | + |
| 17 ($1 \times 10^4$ copies of pafzeliiLN) | + | + | + | + | + | + |
| 18 ($1 \times 10^4$ copies of pafzeliiLN) | + | + | + | + | + | + |

*"–" indicates the absence of DNA of *Borrelia afzelii* in the sample.
**"+" indicates the presence of DNA of *Borrelia afzelii* in the sample.

Example 5

Specificity of the PCR Using a Different Set of Primers Directed to the p24 Gene in *Borrelia afzelii*

(a) Nucleotide Sequences for a Second Set of Primers and Hybridization Probes

To further illustrate that primers directed against p24 gene is specific for *Borrelia afzelii* in a PCR reaction, an additional primer set (e.g., forward primer, and reverse primer) directed against a different gene in *Borrelia afzelii* was prepared. We designed another primer sets for the p24 gene in *Borrelia afzelii*. The forward and reverse primer was designed using Beacon Designer 4.02 (Build 402003) (PREMIER Biosoft International, Palo Alto, Calif.). The primer sets having the specified nucleotide sequences were purchased from Integrated DNA Technologies (Stokie, Ill.). For this additional primer set, the forward primer has nucleotide sequence set forth in SEQ ID NO: 7 (i.e., 5'-CAGAACTGGA GATGATT-TAA GT-3') (afzelii p24 F2). The reverse primer has nucleotide sequence set forth in SEQ ID NO: 8 (i.e., 5'-ACTTTGAAAA TCTCTTCAT™ GC-3') (afzelii p24 R2). The hybridization probe used in this series of study is identical to that described in Example 1 (i.e., the "the afzelii p24 probe") having a 6-carboxy-fluorescein moiety and a Black Hole Quencher 1 moiety attached to its 5'-end and 3'-end, respectively.

(b) PCR Conditions

PCR was conducted using the similar conditions as described in Example 1. In brief, 25 μl containing the extracted DNA (e.g., 500 ng), 600 nM of the second primer set (i.e., afzelii p24 F2 and azfelii p24 R2) (SEQ ID NOs: 7 and 8), 200 nM of a hybridization probe (nucleotide sequence set forth in SEQ ID NO: 5), and 1×MDL Custom qPCR SuperMix (Quanta BioSciences, Inc., Gaithersburg, Md.). The hybridization probe has a 6-carboxy-fluorescein moiety and a Black Hole Quencher 1 moiety attached to its 5'-end and 3'-end, respectively. 1×MDL Custom qPCR SuperMix has a Quanta BioSciences catalog number of 172-5008, and the 2× stock solution of the SuperMix contained 50 U/ml of AccuStart™ Taq DNA polymerase, 40 mM Tris-HCl (pH 8.4), 100 mM KCl, 6 mM $MgCl_2$, 400 nM dATP, 400 nM dCTP, 400 nM dGTP, 800 nM dUTP, 40 U/ml of UNG, and proprietary stabilizers of Quanta BioSciences, Inc. The reaction mixture was monitored in real-time synthesis of the amplicon resulting from each successful PCR.

(c) Real-Time PCR

Real-Time PCR was conducted using the Rotor-Gene 3000 platform (Corbett Research, Sydney, Australia) and the parameters were in accordance with that described in Example 1 (above). The amplification target for *Borrelia afzelii* is p24 gene, and successful amplification would result in a 128 by amplicon product.

Figure 4:
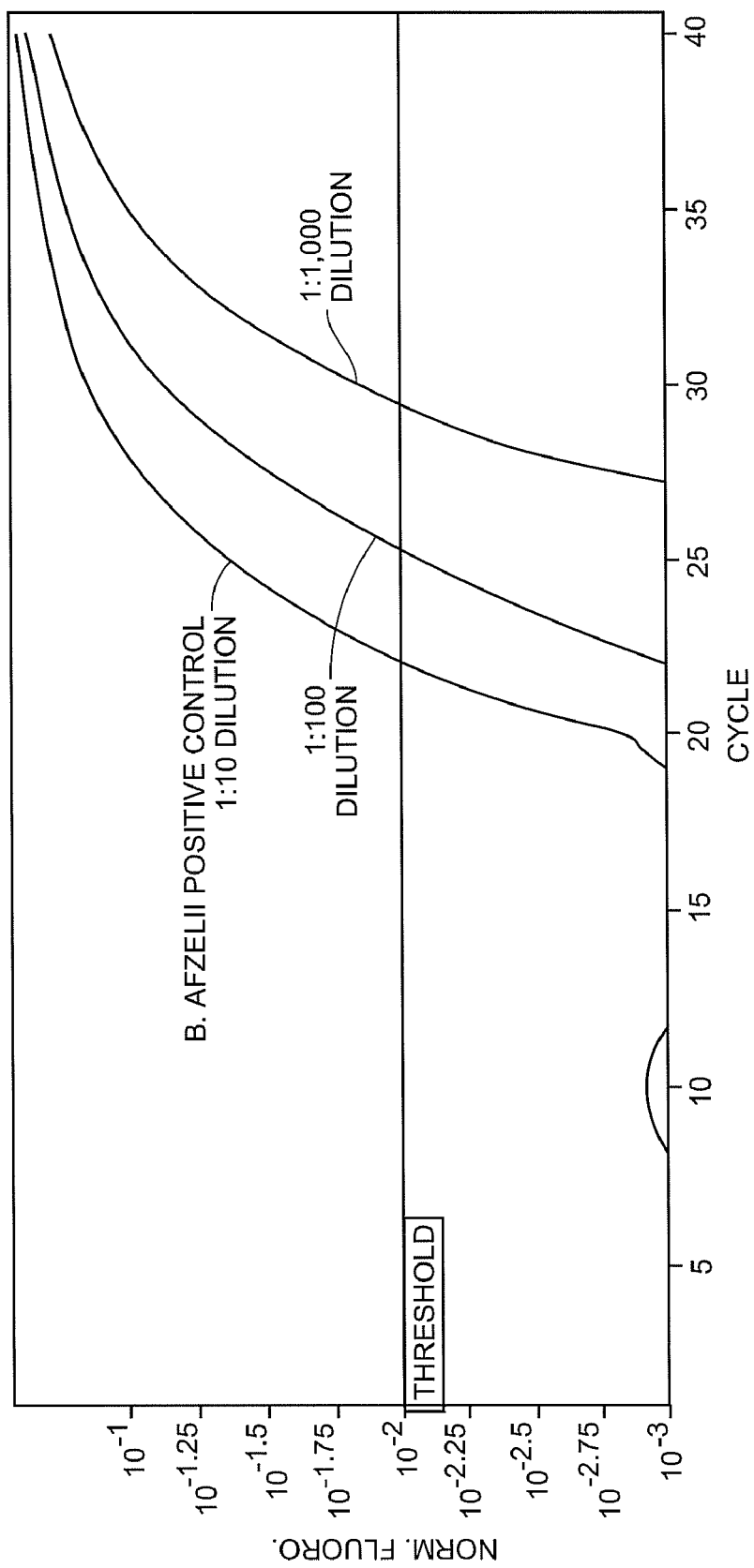
FIG. 4 depicts the *Borrelia afzelii* cross-reactivity analysis of the *Borrelia afzelii* lysK gene by Real-Time PCR. Quantitation data displayed (from left to right) are *Borrelia garinii* (1:10 dilution), *Borrelia burgdorferi* (1:10 dilution), *Borrelia afzelii* (neat), *Borrelia garinii* (1:100 dilution), *Borrelia garinii* (1:1,000 dilution), *Borrelia garinii* (1:10,000 dilution), *Borrelia garinii* (1:100,000 dilution). Amplification of all three *Borrelia* species demonstrates that this PCR lacks the specificity in the detection of *Borrelia afzelii*.

As shown in the FIG. 4, while the primer set (i.e., the afzelii p24 F2 primer and the afzelii p24 R2 primer) provides a successful amplification product for *Borrelia afzelii* in a concentration range of 1:10 dilution of *B. afzelii* positive to 1:1,000 dilution (in a dose-dependent manner). *B. afzelii* positive was obtained from ATCC. In sharp contrast, the same primer set did not detect any amplification products in *B. garinii* (fluorescence level below the Ct-threshold; FIG. 5) and *B. burgdorferi* (fluorescence level below threshold; Table 4). This result indicates that the p24 gene is highly specific for *Borrelia afzelii*.

To further determine the specificity regarding the second primer set with respect to *B. afzelii*, we also tested twenty-two (22) bacterial/viral species using this primer set. Notably, some of the tested species overlapped with that in Table 1 when using the first primer set (See, Table 1, Example 1). No PCR amplification was observed in any of the test species when the second primer set was used, indicating the high specificity and accurate detection of *B. afzelii* using the second primer set. (See, Table 4).

TABLE 4

| Sample Nos. | Samples | PCR Results |
| --- | --- | --- |
| 1 | HPV 16 | –* |
| 2 | *Moraxella catarrhalis* | – |
| 3 | RSV B | – |
| 4 | *Staphyloccocus aureus* | – |
| 5 | HPIV 4B | – |
| 6 | Coronavirus | – |
| 7 | HHV-6B | – |
| 8 | Influenza B | – |
| 9 | HPIV 3 | – |
| 10 | *N. flavescens* | – |
| 11 | *M. mulieris* | – |
| 12 | Rhinovirus 11 | – |
| 13 | Coxsachie A | – |
| 14 | Coxsachie B | – |
| 15 | HTLV-1 | – |
| 16 | *B. microti* | – |
| 17 | *H. pylori* | – |
| 18 | VZV | – |
| 19 | *B. burgdorferi* | – |
| 20 | *E. coli* | – |
| 21 | EBV | – |
| 22 | *B. afzelii* | +** |
| 23 | Negative Control (no template DNA) | – |

*– indicates the absence of PCR amplification in the sample
**+ indicates the presence of PCR amplification in the sample Based on these data, it is concluded that primer sets directed against the p24 gene of *Borrelia afzelii* provide a specific PCR tool to detect *Borrelia afzelii*. The primers provide specific amplification of an amplicon product for *Borrelia afzelii* and not other related species.

Example 6

Percent Identity (% Sequence Identity) Studies: Primer Sets of p24

Different primer sets against p24 gene of *Borrelia afzelii* were designed. The various primer sets have different percent (%) sequence identity (i.e., ranges from 90% to 70% identity) with respect to the SEQ ID NO: 3 and SEQ ID NO: 4. (See, Table 5) A first primer set against the p24 gene of *Borrelia*

*afzelii* was synthesized and it has 90% nucleotide identity (i.e., the forward primer is 90% identical to SEQ ID NO: 3 and the reverse primer is 90% identical to the nucleotide sequence of SEQ ID NO: 4). In this study, the hybridization probe is the same as that in Example 1. A second primer set against the p24 gene of *Borrelia afzelii* was synthesized, which has 80% identity to SEQ ID NO: 3 (i.e., the forward primer is 80% identical to SEQ ID NO: 3 and the reverse primer is 80% identical to SEQ ID NO: 4). A third primer set against the p24 gene of *Borrelia afzelii* was also synthesized, which has 70% identity to SEQ ID NO: 3 (i.e., the forward primer is 70% identical to SEQ ID NO: 3 and the reverse primer is 70% identical to SEQ ID NO: 4).

As shown in FIG. 5, the primer sets (corresponds to 90% identity to SEQ ID NOs: 3 and 4) detected *B. afzelii* at 1:10 dilution and 1:100 dilution in real-time PCR assay, similar to that when primer set having 100% identity of SEQ ID NO: 3 and SEQ ID NO: 4 was used (Table 5). However, the primer set (which has 80% and 70% identity) did not provide the same specificity. (Table 5). This result indicates that insofar as the primer set (i.e., forward primer and reverse primer) against the p24 gene of *Borrelia afzelii* having sufficient identity to anneal to the template nucleic acid during the real-time PCR, the primer set can provide good results and reveal the presence of *Borrelia afzelii*.

35210) was purchased from ATCC source, and subjected to DNA extraction prior to the PCR reaction, as described in Example 1. The primer set has the nucleotide sequences as set forth in Table 6. The primer set was synthesized and used in a real-time PCR with conditions described in Example 1.

TABLE 6

Primer Sequences that targeted against the lysK gene for Class 1 lysyl-tRNA synthetase in Borrelia afzelii

| | |
|---|---|
| afzelii lysK F primer | 5'-ACT CAT GTG AAT GCG AAA ATC AAG-3' (SEQ ID NO: 15) |
| afzelii lysK R primer | 5'-TGC AGG TTC AA GTC AA TTC TTC-3' (SEQ ID NO: 16) |
| afzelii lysK hybridization probe | 5'-/FAM/ TCC ATC TCA TAG GCC AAT CTA TTC TCC AGG/BHQ-1/-3' (SEQ ID NO: 17) |

As shown in the following Table 7, PCR amplification was detected in *B. afzelii*. Fluorescence detection goes as low as 1:100,000 dilutions, indicating that the PCR assay is highly sensitive. However, the PCR amplification was also observed in *B. garinii* and *B. burgdorferi*. These results stand in sharp

TABLE 5

| Primers | Sequences | PCR Results |
|---|---|---|
| 70% identity to afzelii p24 F1 | 5'-CAA GCA AGC AAA GG-3' (SEQ ID NO: 9) | −* |
| 70% identity to afzelii p24 R1 | 5'-AGG CTT TTG ACT GCT C-3' (SEQ ID NO: 10) | − |
| 80% identity to afzelii p24 F1 | 5'-AGC AAG CAA AGG TAT AAG-3' (SEQ ID NO: 11) | − |
| 80% identity to afzelii p24 R1 | 5'-AGG CTT TTG ACT GCT CTC A-3' (SEQ ID NO: 12) | − |
| 90% identity to afzelii p24 F1 | 5'-CAA GCA AGC AAA GGT ATA AGG-3' (SEQ ID NO: 13) | + |
| 90% identity to afzelii p24 R1 | 5'-AGG CTT TTG ACT GCT CTC ATC A-3' (SEQ ID NO: 14) | +** |

*"−" indicates the absence of PCR amplification in the sample
**"+" indicates the presence of PCR amplification in the sample Example 7

Lack of Specificity of the PCR: Using Primers Against an Another Gene (i.e., lysK Gene) in *Borrelia afzelii*

To further illustrate the specificity of the p24 gene in the PCR reaction, we designed primer set directed against a different gene (i.e., the lysK gene) in *Borrelia afzelii*. The lysK gene for class 1 lysyl-tRNA synthetase in *Borrelia afzelii* contains 1,566 by nucleotides; and the GeneBank accession number for the lysK nucleotide sequence is AJ416851. In this experiment, the specificity of the PCR utilizing the combination of the afzelii lysK F primer, afzelii lysK R primer, and the afzelii lysK hybridization probe was assessed by attempting to conduct PCRs with different *Borrelia* species (i.e., *B. afzelii*, *B. garinii*, and *B. burgdorferi*). Each pathogen (i.e., *Borrelia afzelii*: ATCC® No. 51567; *Borrelia garinii*: ATCC® No. 51383; and *Borrelia burgdorferi*: ATCC® No.

contrast as compared to the primer sets (directed against the p24 gene) when they are used. Unlike the lysK gene, prime sets against the p24 gene are highly specific for *B. afzelii*. While the PCR amplification of the lysK gene provides cross-reactivity to two related species of *Borrelia* (i.e., *B. garinii* and *B. burgdorferi*), the PCR amplification of the p24 gene is specific only *B. afzelii* and does not cross-react to the 48 pathogens tested so far (see Table 1).

TABLE 7

| Sample Nos. | Samples | Results |
|---|---|---|
| 1 | *B. afzelii* (neat) | +** |
| 2 | *B. afzelii* (1:10) | + |
| 3 | *B. afzelii* (1:100) | + |
| 4 | *B. afzelii* (1:1,000) | + |
| 5 | *B. afzelii* (1:10,000) | + |
| 6 | *B. afzelii* (1:100,000) | + |
| 7 | *B. garinii* (1:10) | + |

TABLE 7-continued

| Sample Nos. | Samples | Results |
|---|---|---|
| 8 | *B. garinii*(1:100) | + |
| 9 | *B. burgdorferi* (1:10) | + |
| 10 | *B. burgdorferi* (1:100) | + |
| 11 | Negative Control (no template DNA) | −* |

*− indicates the absence of PCR amplification in the sample.
**+ indicates the presence of PCR amplification in the sample.

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of detecting the presence of *Borrelia afzelii* in a biological sample, comprising:
   (a) mixing
      (i) DNA extracted from said biological sample,
      (ii) a primer pair comprising a forward primer and a reverse primer that target a p24 gene of *Borrelia afzelii*, and
      (iii) a hybridization probe, in a PCR vessel, wherein said hybridization probe comprises a fluorescent moiety;
   (b) amplifying said mixture of step (a), in a real-time PCR reaction, under conditions to allow production of an amplicon; and
   (c) detecting a presence or absence of *Borrelia afzelii*, by detecting a presence or absence of a fluorescent signal resulting from the formation of said amplicon, wherein the presence of a fluorescent signal is indicative of the presence of *Borrelia afzelii*,
wherein said forward primer consists of nucleotide sequence 453-474 set forth in SEQ ID NO: 1, said reverse primer consists of nucleotide sequence 74-95 set forth in SEQ ID NO: 2, and said hybridization probe consists of nucleotide sequence 492-521 of SEQ ID NO: 1.

2. A kit for PCR detection of *Borrelia afzelii*, comprising:
(a) a forward primer that consists of nucleotides 453-474 of SEQ ID NO: 1;
(b) a reverse primer that consists of nucleotides 74-95 of SEQ ID NO: 2; and
(c) a hybridization probe that consists of nucleotides 492-521 of SEQ ID NO: 1.

* * * * *